US00PP37109P2

(12) United States Plant Patent
Yencho et al.

(10) Patent No.: US PP37,109 P2
(45) Date of Patent: Nov. 25, 2025

(54) SWEETPOTATO PLANT NAMED 'NCORNSP-034SCVPG'

(50) Latin Name: *Ipomoea batatas*
Varietal Denomination: NCORNSP-034SCVPG

(71) Applicant: North Carolina State University, Raleigh, NC (US)

(72) Inventors: George Craig Yencho, Raleigh, NC (US); Kenneth Vincent Pecota, Raleigh, NC (US); Christopher Heim, Morrisville, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 19/093,545

(22) Filed: Mar. 28, 2025

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — Myers Bigel, P.A.

(57) ABSTRACT

'NCORNSP-034SCVPG' is a moderately compact, non-twining, semi-upright variety producing many short shoots. It is distinguishable from other cultivars on the market by its purple and green variegated cordate leaves. 'NCORNSP-034SCVPG' also exhibits good vigor and is well branched, a growth habit that promotes good plant production in the greenhouse for wholesale distributors. In greenhouse and field trials, 'NCORNSP-034SCVPG' has been shown to have stable variegation and is suitable for use as a landscape or containerized plant.

7 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'NCORNSP-034SCVPG'.

BACKGROUND OF THE INVENTION

*Ipomoea batatas* is a member of the morning glory family Convolvulaceae. This species is grown worldwide and it exhibits a wide range of plant forms and colors. The cultivated members of *Ipomoea batatas* grown by farmers worldwide are commonly produced for consumption of their nutritious, enlarged storage roots. These types typically produce a fast-growing green vine that has a wide variety of leaf shapes ranging from palmate and deeply lobed, to cordate or triangular shaped leaves with no lobes.

Like their edible forms, *Ipomoea batatas* ornamental sweetpotato plants are a heat-loving, drought-tolerant, perennial vine typically grown as an annual. However, ornamental sweetpotato plants are distinguished from the edible cultivated forms in that they often do not produce attractive, enlarged storage roots suitable for human consumption. Instead, they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g., pale yellow to dark purple with some exhibiting temporal and individual leaf color variegation patterns) and plant shapes (e.g., mounded and very compact to prostrate and highly spreading). They can be grown in a potted plant and/or mixed planting format, they can cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

To meet the growing horticultural demand for ornamental sweetpotatoes, it is desirable to produce new cultivars of ornamental sweetpotato with new or improved foliage colors, variegation patterns, leaf shapes, and plant architectures. In addition, it would be advantageous to develop cultivars of ornamental sweetpotato exhibiting a more compact growth that do not out- compete other species in mixed containers.

'NCORNSP-034SCVPG' was bred to meet the increasing demand for new ornamental sweetpotatoes. 'NCORNSP-034SCVPG' is a moderately compact, non-twining, upright variety. It is distinguishable from other cultivars by its heart-shaped leaves, which showcase a purple and green variegation. The purple and green variegated leaves, vigor, and plant architecture, which promotes good plant production in the greenhouse for wholesale distributors, distinguishes 'NCORNSP-034SCVPG' amongst the current ornamental sweetpotatoes in the marketplace. 'NCORNSP-034SCVPG' exhibits very good vigor and is well branched. Additionally, unlike many variegated lines, 'NCORNSP-034SCVPG' has a low reversion rate, maintaining its variegation well in propagation and in the garden. In greenhouse and field trials conducted since 2022 by the breeding program and industry collaborators, 'NCORNSP-034SCVPG' has been shown to be much more compact than *Ipomoea batatas* 'Tricolor' (unpatented; also known as 'Pink Frost') and 'Sweet Caroline Green Yellow' (U.S. Plant Pat. No. 18,673) and is suitable for use as a landscape or containerized plant. 'NCORNSP-034SCVPG' has not been observed to produce flowers during evaluation periods.

Lineage. 'NCORNSP-034SCVPG' (breeding designation NC10564-003ORN) originated from hand-pollinated seed from the proprietary *Ipomoea batatas* breeding lines NC9802-004ORN (the female parent; not patented) and NC10433-007ORN (the male parent; not patented). Botanical seed was harvested from ornamental lines grafted onto a flower-inducing *Ipomoea setosa* sweetpotato line (unnamed) in greenhouses between October 2021 and April 2022 in Raleigh, North Carolina. NC9802-004ORN resulted from hand-pollinated seed harvested from the proprietary *Ipomoea batatas* breeding line NC1835-001ORN (the female parent; not patented) and NC6879-008ORN (the male parent; not patented). NC10433-007ORN resulted from hand-pollinated seed collected from NC9808-024ORN (the female parent; not patented) and NC9802-001ORN (the male parent; not patented). Botanical seeds from this family were planted in the greenhouse in late winter 2022. The first cycle of selection on the population was exercised at the seedling tray stage and each survivor was transferred to a single 6-inch pot, which was then maintained in the greenhouse. Cuttings (2 each) were taken from the plants in April and planted in the field as unreplicated 2-plant plots, during mid-June 2022. The single, individual plant now known as 'NCORNSP-034SCVPG' was selected in September 2022 because of its combination of exceptional features, and it has been propagated asexually since that time.

Asexual Reproduction. Since its selection, *Ipomoea batatas* 'CORNSP-034SCVPG' has been asexually reproduced in Raleigh, North Carolina predominantly by vegetative propagation of vine cuttings. Successively, there have been six cycles of vegetative propagation, one cycle of tissue culture micropropagation, and multiple vegetative propagation cycles to increase plant numbers. Asexual reproduction of 'NCORNSP-034SCVPG' by cuttings has shown that the unique features of the new cultivar are stable, and the plant reproduces true to type in successive generations.

SUMMARY OF THE INVENTION

'NCORNSP-034SCVPG' is a moderately compact, non-twining, semi-upright variety. It is distinguishable from other cultivars by its heart-shaped leaves with purple and green mottled variegation. The purple and green variegation distinguishes 'NCORNSP-034SCVPG' amongst the current ornamental sweetpotatoes in the marketplace. 'NCORNSP-034SCVPG' also exhibits good vigor and is well branched, a growth habit that promotes good plant production in the greenhouse for wholesale distributors. In greenhouse and field trials conducted since 2022 by the breeding program and industry collaborators, 'NCORNSP-034SCVPG' has been shown to be a much more compact than *Ipomoea batatas* 'Tricolor' and 'Sweet Carolina Green Yellow' and is suitable for use as a landscape or containerized plant. 'NCORNSP-034SCVPG' has not been observed to produce flowers during the trial period.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which more accurately describe the colors of the new *Ipomoea batatas*.

DETAILED BOTANICAL DESCRIPTION OF THE NEW VARIETY

The following is a detailed description of the botanical characteristics of a new and distinct cultivar of *Ipomoea batatas* plant known by the cultivar name 'NCORNSP-034SCVPG'. All colors cited herein refer to The Royal Horticulture Society Colour Chart designations (The Royal Horticultural Society, London, 2001, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134 pp.). Where dimensions, sizes, colors, and other characteristics are given, it is to be understood that such characteristics are approximations or averages set forth as accurately as practicable.

The descriptions reported herein are from a group of 73-day-old specimens grown individually in six-inch azalea pots. The plants were grown in Raleigh, North Carolina, under commercial practice in a glass-covered greenhouse, where, during the summer, day and night temperatures range between 30-40° C. and 22-26° C., respectively. After rooting, plants were treated with 200 ppm 20-10-20 fertilizer weekly. Plant measurements were taken in September 2024 at the Horticulture Field Lab (HFL) in Raleigh, North Carolina. *Ipomoea batatas* 'NCORNSP-034SCVPG' has not been observed under all possible environmental conditions; therefore, the phenotype may vary under different environmental conditions such as season, temperature, light intensity, day length, cultural conditions, and the like, without however, any variance in the genotype.

Classification:

*Botanical name.*—*Ipomoea batatas* (L.) Lam.

*Common name.*—Ornamental Sweetpotato.

*Variety name.*—'NCORNSP-034SCVPG'.

Growth conditions: *Ipomoea batatas* 'NCORNSP-034SCVPG' has very good vigor and a moderate growth rate. In locations with mild winter conditions, *Ipomoea batatas* 'NCORNSP-034SCVPG' will grow perennially; otherwise, it is an annual plant. Similar to other cultivated sweetpotatoes, wind or rain rarely causes much damage to 'NCORNSP-034SCVPG', but if damage does occur, the plant drops the damaged leaves and grows new shoots at nodes where the leaves were lost. Under low light levels in a greenhouse, 'NCORNSP-034SCVPG' can develop intumescence, which will remain on the affected foliage, but will be outgrown with new foliage.

Figure 1A:
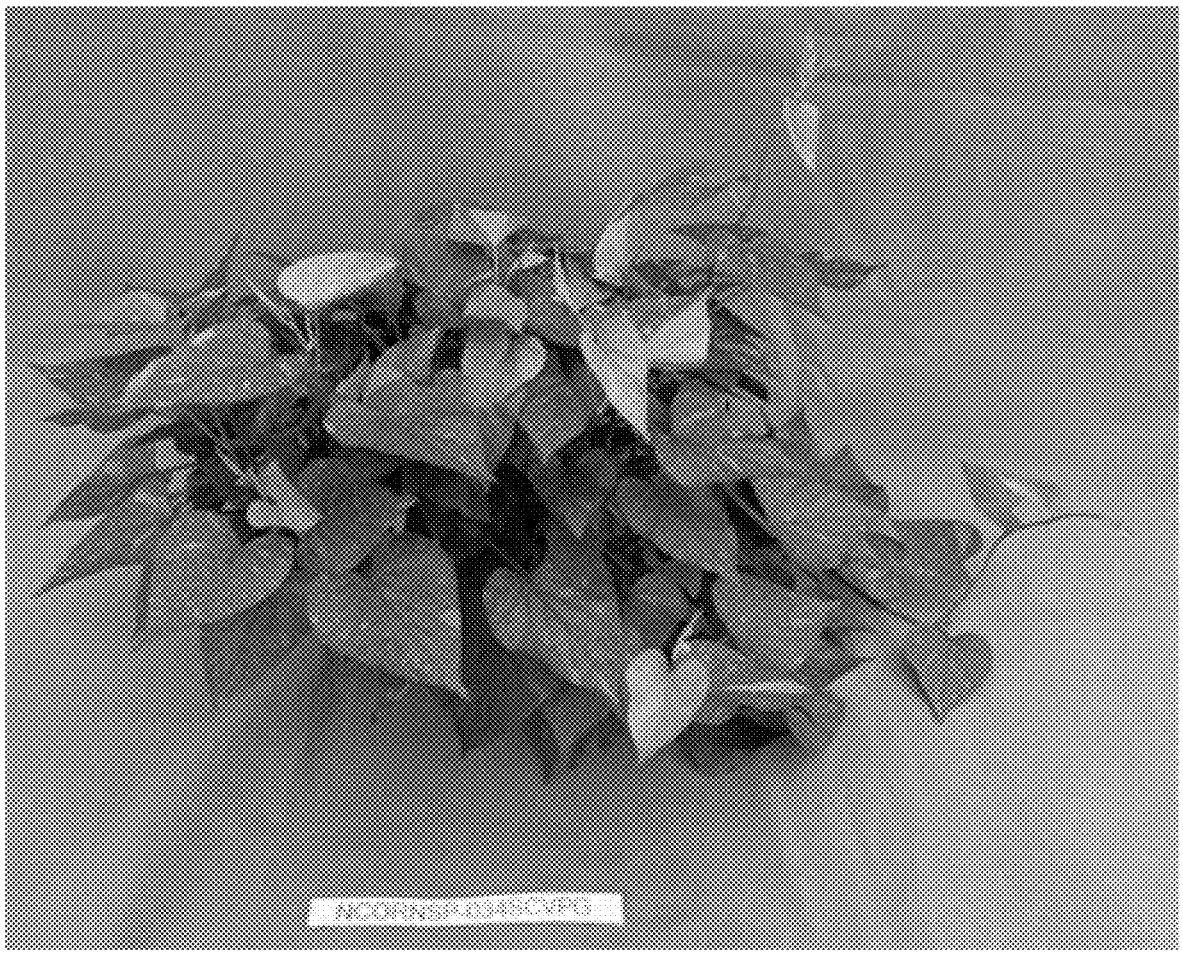
FIGS. 1A-1B are color photographs of a typical specimen of greenhouse grown *Ipomoea batatas* 'NCORNSP-034SCVPG' in a 6-inch pot from the side (FIG. 1A) and top (FIG. 1B), 55 days after planting.
Figure 1B:
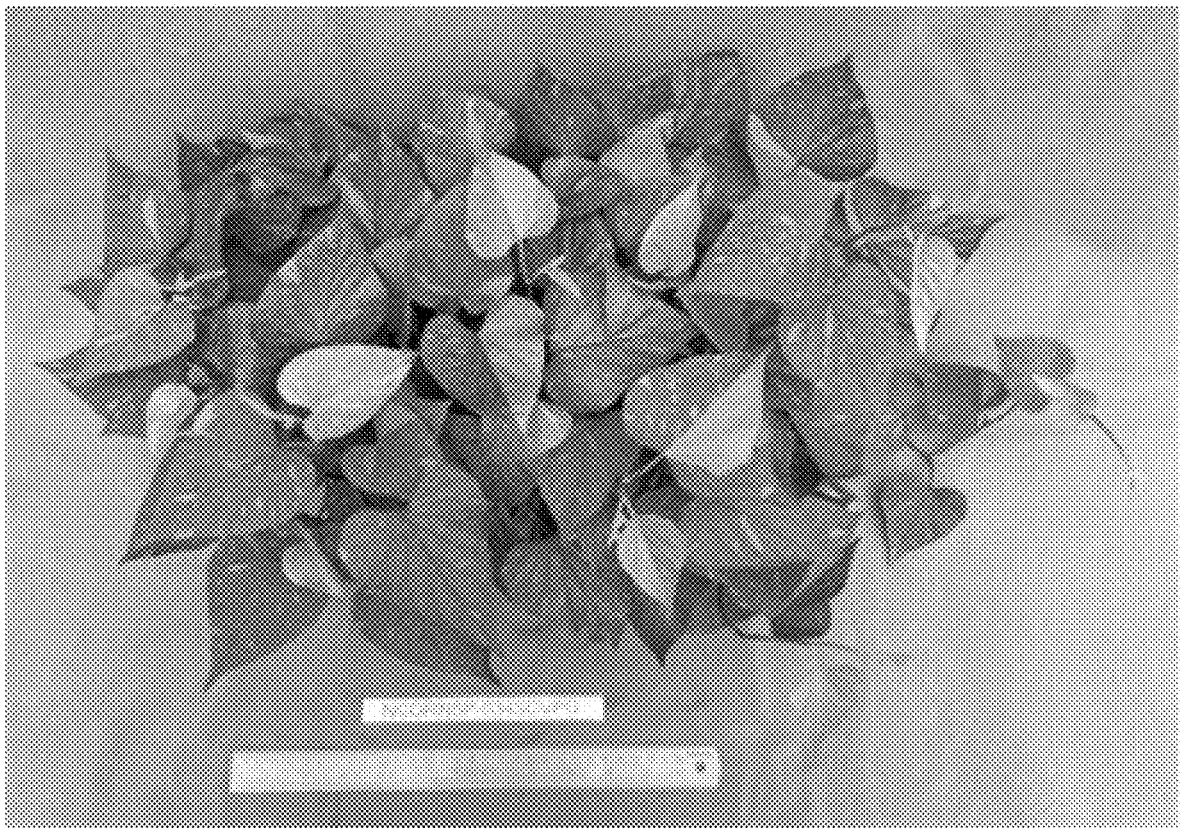
Figure 2A:
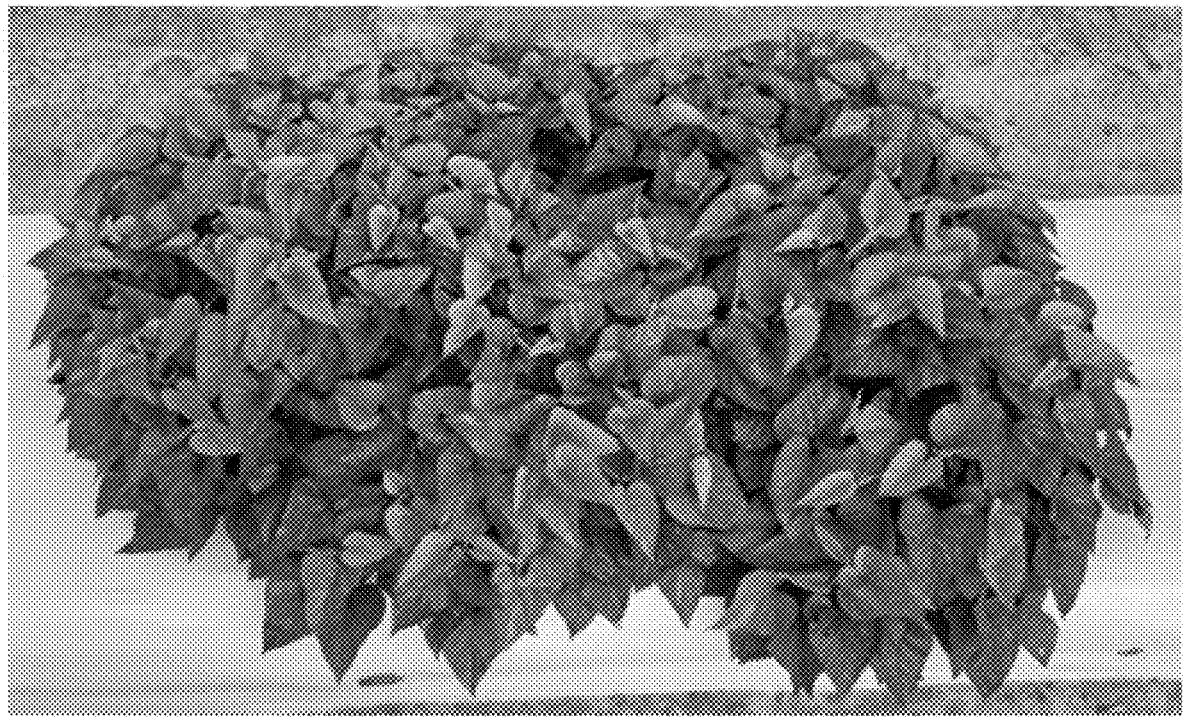
FIGS. 2A-2B are color photographs of a typical specimen of *Ipomoea batatas* 'NCORNSP-034SCVPG' from side (FIG. 2A) and top (FIG. 2B) in the field, 74 days after planting.
Figure 2B:
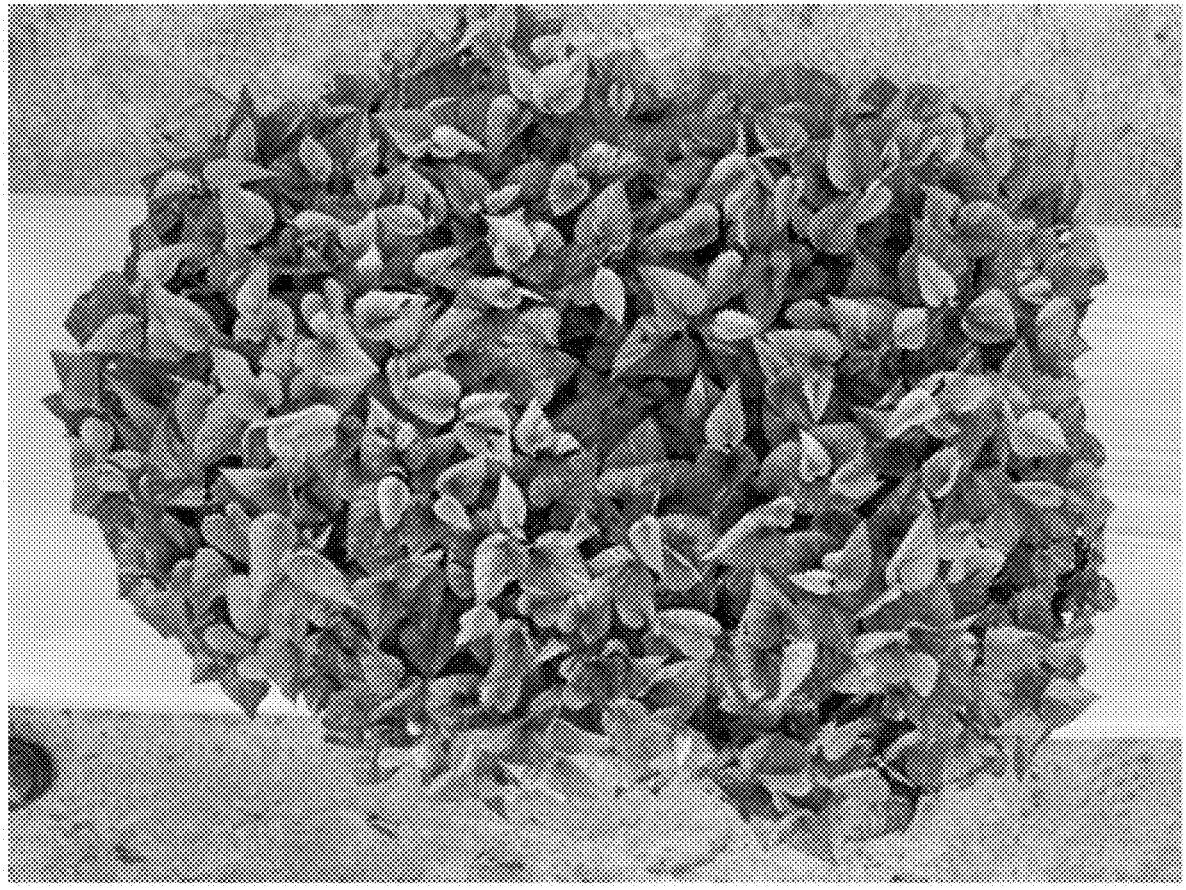
Figure 3A:
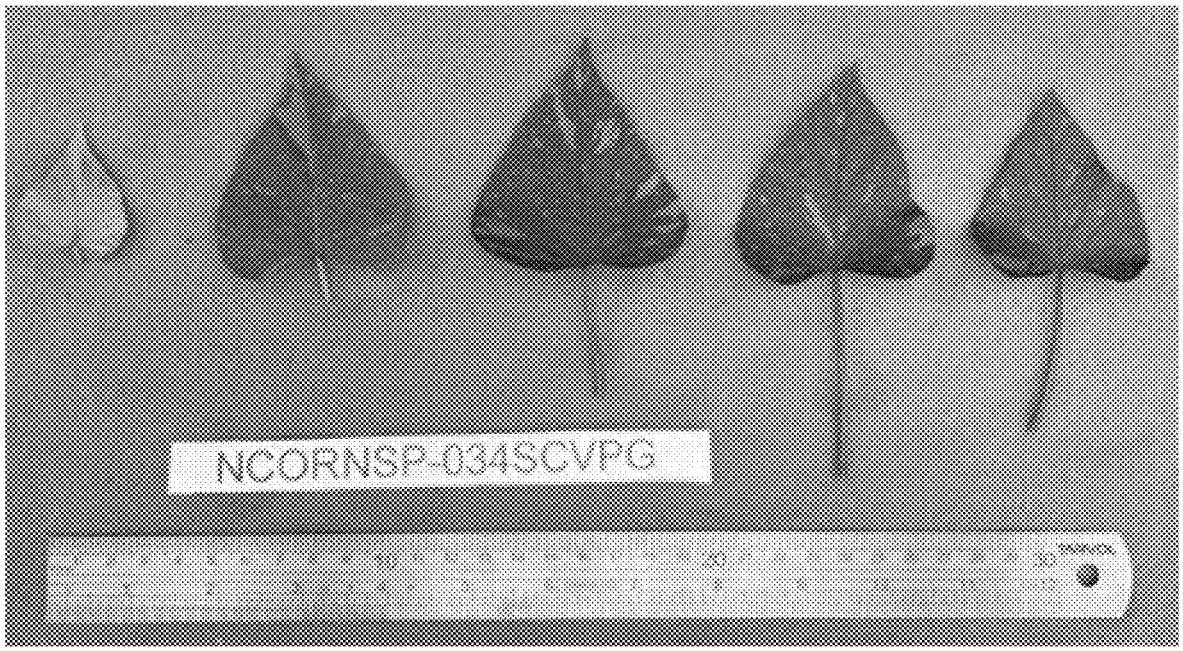
FIGS. 3A-3B are color photographs showing the upper (FIG. 3A) and lower (FIG. 3B) surfaces of mature leaves produced by *Ipomoea batatas* 'NCORNSP-034SCVPG', 55 days after planting.
Figure 3B:
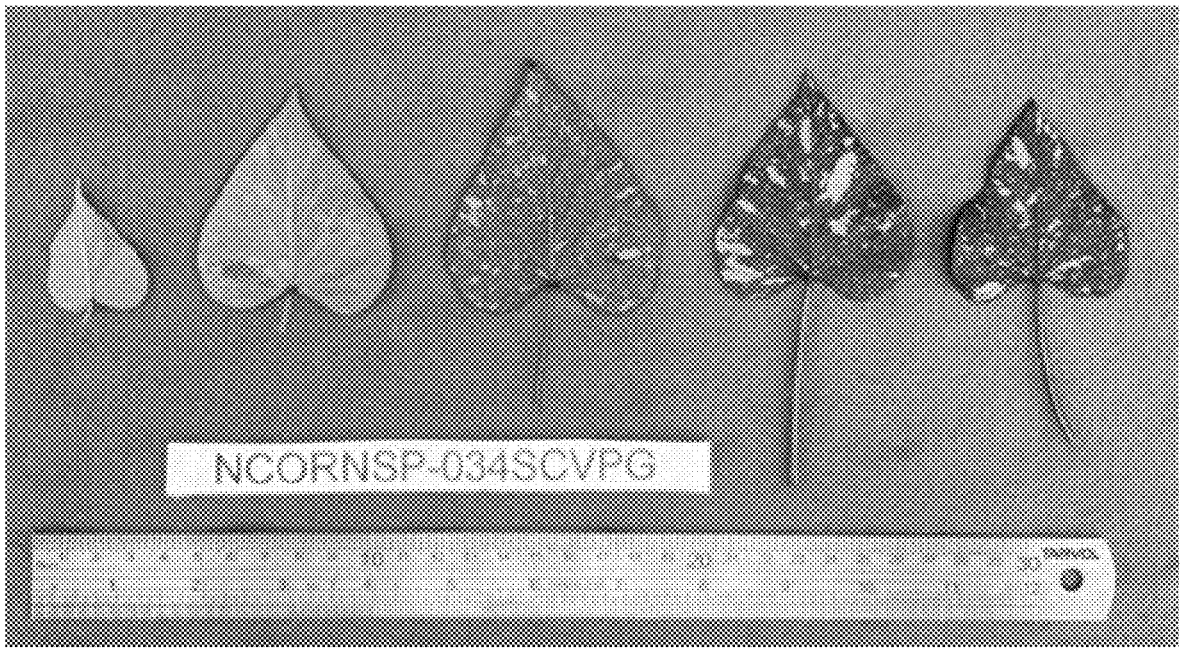
Figure 4A:
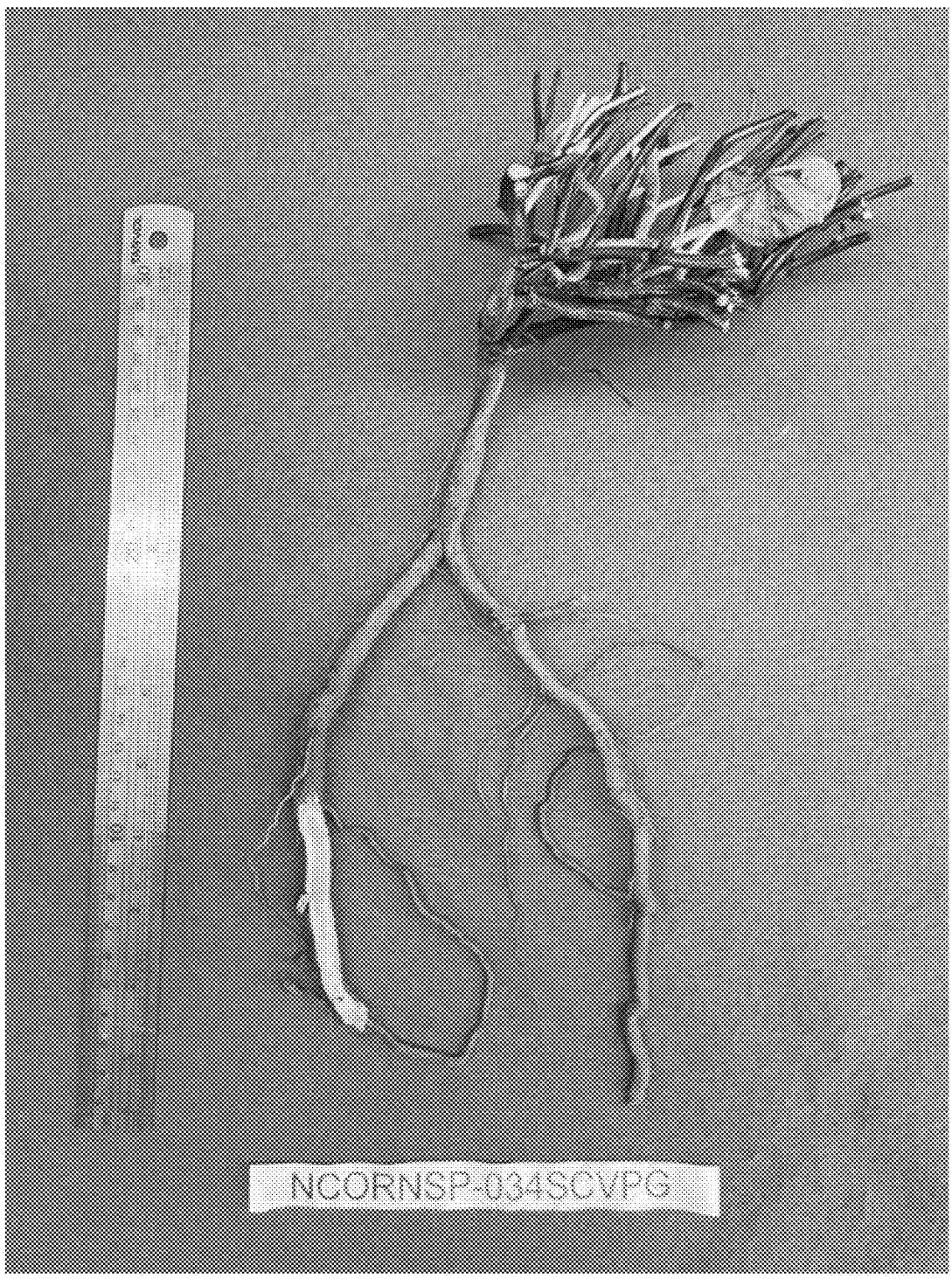
FIGS. 4A-4B are color photographs showing the storage roots produced by *Ipomoea batatas* 'NCORNSP-034SCVPG' in the field, 126 days after planting.
Figure 4B:
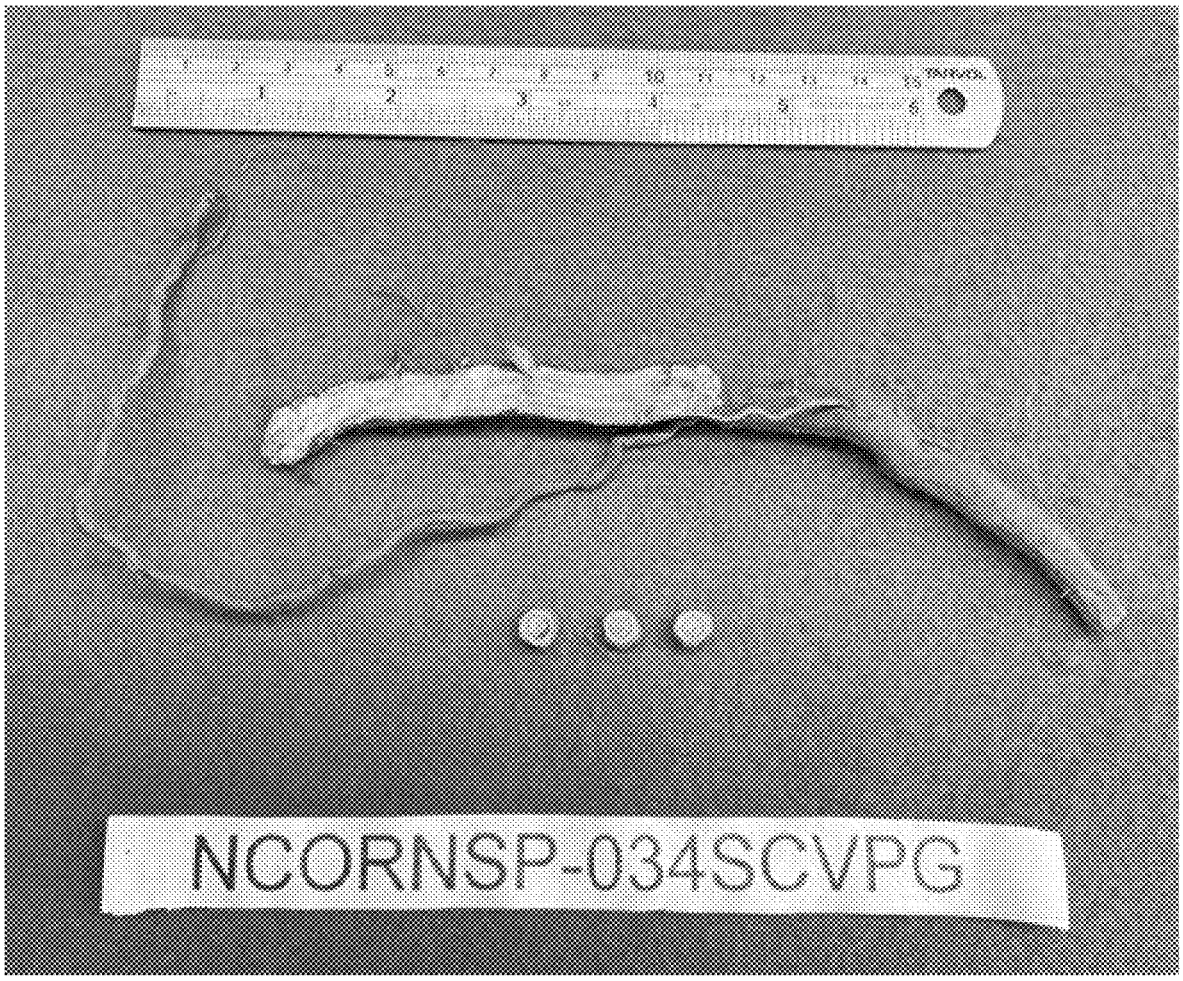

Aboveground structure and coloration: FIGS. 1A, 1B, 2A, 2B, 3A and 3B show the shape and coloration of a typical specimen of *Ipomoea batatas* 'NCORNSP-034SCVPG'. Color may vary somewhat due to temperature and nutrient stress. Overall, this cultivar is a moderately compact, non-twining, semi-upright herbaceous plant that has an average height of 23±4.3 cm and an average area spread of 59±8.2 cm. The growth habit of this plant is upright with shoots growing upward and outward.

Branches:

*Branching habit*.—Freely-branching with about 9-10 primary lateral branches coming off the stem. Dense foliage and no pinching is required to stimulate branching. Branch texture is smooth and glabrous with slight pubescence.

*Vegetative lateral branching*.—Length: 18.8±6.5 cm. Diameter: 0.2±0.01 cm. Internodes have an average length of 4.1±0.4 cm.

*Secondary lateral shoots*.—No measurable secondary lateral shoots formed on the rated plants.

*Stem*.—Round and slightly glabrous with an upward, very strong, slightly flexible, non-brittle strength. Primary color: maroon (RHS N186C). Secondary color: light green (RHS 145C).

*Adventitious roots*.—Absent at nodes.

Foliage: Leaves are alternate and tend to slightly spiral around the stem. They are simple and deltoid in shape. (see FIGS. 3A-3B).

*Quantity*.—Heavily foliated, with approximately 20±8 leaves per lateral branch.

*Mature leaf length*.—7.2±0.9 cm.

*Mature leaf width*.—6.3±1.3 cm.

*Leaf margin*.—Entire.

*Leaf apex*.—Acuminate.

*Leaf base*.—Cordate.

*Leaf texture*.—Glabrous texture and matte finish.

*Venation*.—Palmate. Texture: Glabrous.

*Color*.—Mature leaves are greyed-purple (RHS N186A) and green (RHS 137A) and typically range in color within the green RHS 137A to 137C color codes. See also Table 1.

*Petiole*.—Petioles are held slightly upward and curve outward. Leaf petiole has a smooth glabrous texture. Length: 8.5±1.6 cm. Diameter: 0.2±0.02 cm. Primary color: Greyed-purple (RHS 183B). Secondary color: yellow-green (RHS 147B).

TABLE 1

Leaf color of *Ipomoea batatas* 'NCORNSP-034SCVPG.'

| Leaf Structure | Upper (Adaxial) Surface | Lower (Abaxial) Surface |
|---|---|---|
| Mature Leaf | Greyed-Purple, Green (RHS N186A, 137A) | Purple, Green (RHS N79A, 138B) |
| Young Leaf | Yellow-Green (RHS 144A) | Yellow-Green (RHS 144A) |
| Vein - mature leaf | Greyed-purple, Green (RHS N186A, 137A) | Purple (RHS N79B) |
| Vein - young leaf | Yellow-Green (RHS 144A) | Green (RHS 138B) |

Inflorescence: The production of flowers by 'NCORNSP-034SCVPG' is very sporadic and mostly observed under stressful conditions (e.g., drought, nutrient stress, cloudy weather). Shorter day lengths enhance flowering, but the precise photoperiod for flower induction is currently unknown. Solitary, regular funnel-form flowers arising from leaf axils on secondary lateral branches are formed. Peduncles are purple (RHS N186C) and green (RHS 145B). Peduncle length: about 2.2 cm, peduncle diameter: about 0.2 cm. Flower buds are purple (RHS 187A) and green (RHS 145B) and elliptic. Limb color: Pinkish (RHS 76A, 76B) on the outer surface and inner surface. The outer throat color begins purple (RHS 77A) and gradually lightens toward the limb. The limb is pentagonal to rounded with slight fragrance. Corolla length: about 4.5 cm, corolla width: about 3.6 cm. The flower averages five sepals. The outer sepals are shorter than the inner sepals. Average outer sepal length: about 1.0 cm, average outer sepal width: about 0.4 cm, average inner sepal length: about 1.1 cm, average inner sepal width: about 0.4 cm. The sepals are elliptic with an acute apex and smooth margins and are purple (RHS 187A) and green (RHS 145B) in color. A single pistil consists of one style and one stigma and is about 2.1 cm in length. Stigma and style are both cream (RHS N155B). The stigma is exerted relative to the stamens. The flower averages five stamens. Pollen color: cream (RHS N155D). Pollen production is low but variable. Fruit has not been observed under normal greenhouse conditions.

Storage root coloration: Plants form no, to small, underground storage roots that are typically malformed and do not meet USDA Sweetpotato Storage Root Grade Standards (see FIGS. 5A-5B). Fibrous roots are typically yellow-white (RHS 158A). Storage roots that are formed possess greyed-purple (RHS 184A) skin.

Disease or pest resistance: 'NCORNSP-034SCVPG' is susceptible to whiteflies and thrips in a greenhouse environment. 'NCORNSP-034SCVPG' is susceptible to damage by Japanese beetles (*Popillia japonica*) under outdoor conditions. Its resistance or susceptibility to other known insects and pathogens of sweetpotato are unknown. Under low light conditions, slight edema may occur.

Comparison with other *Ipomoea batatas* cultivars: 'NCORNSP-034SCVPG' is distinct based on leaf color and variegation. Of the common cultivars of ornamental sweetpotato, 'NCORNSP-034SCVPG' is best compared with the 'Pink Frost' (unpatented) and 'Sweet Caroline Green Yellow' (U.S. Plant Pat. No. 18,673) cultivars (Table 2). Like both 'Pink Frost' and 'Sweet Caroline Green Yellow,' 'NCORNSP-034SCVPG' is variegated. However, 'NCORNSP-034SCVPG' showcases purple and green variegation, which is not seen in either comparison line. 'NCORNSP-034SCVPG' also has cordate leaves, differentiating itself from both 'Pink Frost' and 'Sweet Caroline Green Yellow.' The habit of 'NCORNSP-034SCVPG' is more compact than either 'Pink Frost' or 'Sweet Caroline Green Yellow'.

'NCORNSP-034SCVPG' is distinct from its parents 'NC9802-004ORN' and 'NC10433-007' by its lack of leaf lobing and its highly variegated patterning. 'NCORNSP-034SCVPG' has no lobes, compared to parents 'NC9802-004ORN' (5 lobes) or 'NC10433-007ORN' (3 lobes). 'NCORNSP-034SCVPG' shares some of its parent's compactness.

TABLE 2

Comparison of 'NCORNSP-034SCVPG' with other *Ipomoea batatas* cultivars.

| Characteristic | 'NCORNSP-034SCVPG' | 'Pink Frost' (Unpatented) | 'Sweet Caroline Green Yellow' (U.S. Plant Pat. No. 18,673) |
|---|---|---|---|
| Plant Habit | Moderately compact, semi-upright and mounding habit | Trailing habit with low branching | Trailing with low branching |
| Average Leaf Length and Width | Length: 7.2 cm Width: 6.3 cm | Length: 7.5 cm Width: 8.7 cm | Length: 7 cm Width: 8.5 cm |
| Foliage Color | Greyed-purple, Green (RHS N186A, 137A) | Green, White (137C, N155B) | Green (RHS147A), with irregular flecks and streaks (145B, 146C) |

TABLE 2-continued

Comparison of 'NCORNSP-034SCVPG' with other *Ipomoea batatas* cultivars.

| Characteristic | 'NCORNSP-034SCVPG' | 'Pink Frost' (Unpatented) | 'Sweet Caroline Green Yellow' (U.S. Plant Pat. No. 18,673) |
|---|---|---|---|
| Leaf Shape | Cordate leaf. Entire with a cuspidate apex and a cordate base. | Triangular to semi-elliptic, lobing variable from zero to many | Moderate to deeply lobed, 3-5 lobes. Entire with an acuminate apex and a lobed base |

We claim:

1. A new and distinct cultivar of *Ipomoea batatas* plant named 'NCORNSP-034SCVPG'substantially as illustrated and described herein.

* * * * *